United States Patent
Arnitz et al.

(10) Patent No.: US 9,920,970 B2
(45) Date of Patent: Mar. 20, 2018

(54) FLEXIBLE CRYOGENIC CONTAINER SYSTEM

(75) Inventors: Theo Arnitz, Waghäusel (DE); Carsten Liebig, Mannheim (DE)

(73) Assignee: HOFFMANN-LA ROCHE, INC., Nutley, NJ (US)

( * ) Notice: Subject to any disclaimer, the term of this patent is extended or adjusted under 35 U.S.C. 154(b) by 665 days.

(21) Appl. No.: 13/183,045

(22) Filed: Jul. 14, 2011

(65) Prior Publication Data
US 2011/0309086 A1    Dec. 22, 2011

Related U.S. Application Data

(63) Continuation of application No. PCT/EP2010/000117, filed on Jan. 13, 2010.

(30) Foreign Application Priority Data

Jan. 20, 2009  (EP) .................................... 09150937

(51) Int. Cl.
*F25D 25/00* (2006.01)
*F25D 3/10* (2006.01)
(Continued)

(52) U.S. Cl.
CPC .......... *F25D 3/105* (2013.01); *A01N 1/0257* (2013.01); *A01N 1/0263* (2013.01);
(Continued)

(58) Field of Classification Search
CPC .................. F25D 3/105; F25D 31/006; F25D 2303/0841; F25D 3/107; F25D 2331/8014;
(Continued)

(56) References Cited

U.S. PATENT DOCUMENTS 3,893,834 A * 7/1975 Armstrong ................ F25D 5/02
62/4
4,049,408 A * 9/1977 Patel ........................ F25D 5/02
206/219
(Continued)

FOREIGN PATENT DOCUMENTS

DE     101 51 343 A1    5/2003
EP       1 441 585 B1    5/2006
(Continued)

OTHER PUBLICATIONS

"Advantages and Disadvantages of Corrugated Cardboard Boxes" by Atlas Box & Crating Company retrieved from https://atlasbox.wordpress.com/2012/09/; retreived on Aug. 17, 2016.*

*Primary Examiner* — Orlando E Aviles Bosques
(74) *Attorney, Agent, or Firm* — Bose McKinney & Evans LLP (57) ABSTRACT

The invention relates to a cryogenic container for storing and/or transporting a medium, in particular a biochemical and/or medical product. The cryogenic container comprises at least one primary container, which has at least one flexible film bag. The flexible film bag is designed to receive the medium. The cryogenic container furthermore comprises at least one secondary container, which at least partially surrounds the primary container and is preferably at least partially flexible. The secondary container has at least one opening for insertion of the primary container. The secondary container furthermore has at least one preferably at least partially flexible outer sleeve. The secondary container furthermore has at least one heat exchanger space, which is arranged between the outer sleeve and the flexible film bag and receives at least one fluid heat exchange medium.

23 Claims, 4 Drawing Sheets

(51) Int. Cl.
   *A01N 1/02*          (2006.01)
   *F25D 31/00*         (2006.01)

(52) U.S. Cl.
   CPC ............ *A01N 1/0268* (2013.01); *F25D 3/107*
            (2013.01); *F25D 31/006* (2013.01); *F25D*
                                  *2331/8014* (2013.01)

(58) Field of Classification Search
   CPC ... A01N 1/0257; A01N 1/0263; A01N 1/0268
   USPC ................ 62/62, 45.1, 50.1, 50.7, 338, 371,
                 62/373–376, 457.2, 457.9; 220/560.08,
                                              220/592.28
   See application file for complete search history.

(56)         References Cited

U.S. PATENT DOCUMENTS

| | | | | |
|---|---|---|---|---|
| 4,420,097 | A | * | 12/1983 | Motsenbocker .......... A45F 3/16 |
| | | | | 62/457.1 |
| 4,605,006 | A | * | 8/1986 | Jacques .................. A61B 19/00 |
| | | | | 607/113 |
| 4,723,974 | A | * | 2/1988 | Ammerman ........................ 62/4 |
| 5,345,995 | A | * | 9/1994 | Yano ....................... E04B 1/942 |
| | | | | 165/46 |
| 5,943,876 | A | | 8/1999 | Meyer et al. |
| 6,065,625 | A | * | 5/2000 | Bonerb et al. ................. 220/1.5 |
| 6,119,465 | A | * | 9/2000 | Mullens et al. ................... 62/60 |
| 6,301,961 | B1 | * | 10/2001 | Rolfes et al. .................... 73/328 |
| 6,612,125 | B1 | * | 9/2003 | Gevargis ............... F24F 5/0035 |
| | | | | 62/259.1 |
| 6,648,168 | B2 | * | 11/2003 | Fujii et al. ............... 220/592.21 |
| 6,655,156 | B1 | * | 12/2003 | Miksic et al. ................. 62/48.1 |
| 6,668,579 | B1 | * | 12/2003 | Bigwood et al. ............ 62/457.6 |
| 6,708,502 | B1 | * | 3/2004 | Aceves et al. ................. 62/45.1 |
| 7,104,074 | B2 | | 9/2006 | Voute et al. |
| 7,331,192 | B2 | * | 2/2008 | Kummeth et al. .............. 62/371 |
| 7,464,567 | B1 | * | 12/2008 | Crossley et al. ............. 62/457.8 |
| 7,469,548 | B2 | * | 12/2008 | Brunner et al. ................. 62/135 |
| 7,618,584 | B2 | | 11/2009 | Lampeter et al. |
| 7,641,068 | B2 | * | 1/2010 | Immel et al. ................. 220/560.1 |
| 7,896,199 | B2 | * | 3/2011 | Kaczmarek .......... B65D 75/525 |
| | | | | 137/614.2 |
| 2002/0095946 | A1 | * | 7/2002 | Greene ........................ 62/457.2 |
| 2008/0004594 | A1 | * | 1/2008 | Pahlberg et al. ............. 604/410 |
| 2008/0272146 | A1 | * | 11/2008 | Kaczmarek .......... B65D 75/525 |
| | | | | 222/105 |

FOREIGN PATENT DOCUMENTS

| | | | | |
|---|---|---|---|---|
| GB | 1153472 A | * | 5/1969 | ........... F25D 31/006 |
| JP | 6-036642 U | | 5/1994 | |
| JP | 2002-523316 A | | 7/2002 | |
| WO | WO 91/03934 A1 | | 4/1991 | |
| WO | WO 00/12409 A1 | | 3/2000 | |
| WO | WO 02/16209 A1 | | 2/2002 | |

* cited by examiner

FLEXIBLE CRYOGENIC CONTAINER SYSTEM

RELATED APPLICATIONS

This application is a continuation of PCT/EP2010/000117, filed Jan. 13, 2010, which claims priority to EP 09 150 937.2, filed Jan. 20, 2009, which are hereby incorporated by reference in their entirety.

BACKGROUND

The present invention relates to a cryogenic container that is suitable in particular for storing and/or transporting a medium. The cryogenic container is, in particular, suitable for storing and/or transporting a biochemical and/or medical product. The present invention further relates to a secondary container, for use in a cryogenic container according to the invention, and to a preparation device for storage of a medium. The invention further relates to a method for storing and/or transporting a medium, in particular once again a biochemical product. Such devices and methods can be used in particular in the production and/or supply of pharmaceutical and/or diagnostic products which are generally in liquid form particularly at room temperature, but which are generally frozen for storage and/or transport.

In the production and/or supply of media, in particular media with active substances for diagnostics and/or medical therapy, i.e. in particular medical products and/or pharmaceuticals, suitable handling of the media presents a technical challenge. In many cases, in the pharmaceutical production of, for example, biotechnical materials, the media are frozen for storage and/or transport. Cryogenic vessels, also referred to as cryo vessels, are generally used for the freezing and subsequent thawing. These cryogenic containers are generally solid containers made of stainless steel and having a double casing. The product in the containers is frozen and/or thawed via a silicone oil circuit. However, the demands in respect of the sterility of cryogenic containers of this kind, especially for biotechnical materials, are very high.

A crucial disadvantage of the known technology in this area is that, after the container has finished being used, cleaning and sterilization are needed. This is very time-consuming and expensive. It can also happen that silicone oil escapes at the coupling points where silicone oil is supplied to the silicone oil circuit. In addition, large storage surfaces are required, which entail high capital expenditure. The flexibility needed to meet varying requirements is generally not afforded.

These requirements in respect of sterility generally necessitate that the cryogenic containers are operated in circulation, which entails enormous outlay in terms of transport and storage. In particular, the cryogenic containers, which have a considerable weight (in some cases several hundred kilograms), and which have a large volume of in some cases several cubic meters, have to be kept in storage and transported.

In addition to these reusable cryogenic containers, devices are also known from the prior art in which the medium is introduced into a disposable bag and frozen in the latter. U.S. Pat. No. 7,104,074 and EP 1 441 585 B1, for example, disclose containers for freezing, storing and thawing biopharmaceutical materials, which containers can be received in a supporting frame. In these film containers, the biopharmaceutical material is frozen by means of contact heat transfer to a heat transfer surface.

A disadvantage of this prior art, however, is that containers of this kind have to be designed with comparatively thin walls in order to permit rapid freezing of the biopharmaceutical materials without phase separation. At the same time, however, containers of this kind with thin walls are extremely sensitive to mechanical damage, and therefore, in some cases, it is not possible to ensure that the containers are transported safely, without damage and in a sterile condition. Moreover, complex transport and storage devices are needed to ensure the materials being stored and transported in the frozen state.

SUMMARY

Embodiments incorporating the present invention make available devices and methods for storing and/or transporting media in which the disadvantages of known devices and methods are largely avoided. In particular, the devices and methods are intended to simplify the logistics of storing and/or transporting the media and yet still satisfy the requirements of sterility and safety that are normally imposed in the pharmaceutical production of biotechnical materials.

These advantages are achieved by devices and methods having the features of the independent claims. Advantageous developments of the invention, which can be realized individually or in combination, are set forth in the dependent claims. Devices are proposed, and also methods that can be carried out in particular using the described devices.

A concept incorporated by exemplary embodiments is that a medium is frozen and/or thawed in a heat exchanger, which can preferably be completely disposed of after the process. Another concept is to preferably replace known heat exchange media, such as silicone oil, by less expensive heat exchange media, for example liquid nitrogen as heat transfer medium.

A cryogenic container is proposed for storing and/or transporting a medium, in particular a biochemical and/or medical product. As has been described above, the medium can in particular be liquid at room temperature but can be stored and/or transported in the frozen, i.e. solid state. In particular, the medium can be from the above-described area of medical diagnostics and/or pharmaceutics. It can, in particular, be a medium that has to meet strict demands in terms of purity and/or sterility. The medium used is preferably in the form of biotechnical materials and/or of media comprising such biotechnical materials. However, it is also possible in principle to use other types of media, in particular media that are fluid at room temperature, for example liquid and/or possibly also gaseous media.

In the context of the present invention, the term "container" is repeatedly used. This term is therefore already part, for example, of the term "cryogenic container." Moreover, as is explained in detail below, the cryogenic container comprises at least one primary container and at least one secondary container, i.e. also specific forms of containers. In the context of the present invention, a container, as will be immediately appreciated by a person skilled in the art and as is the case in everyday language, is understood generally as a device which, on the inside, has at least one interior or cavity (both terms are used basically as synonyms in the text below). The interior can, in particular, serve the purpose of ensuring that the optional content of the container, received in the interior, is completely or partially separated from its environment. For this purpose, the container can in particular have at least one container wall, preferably a substantially closed container wall, which can provide this separation from the environment and which at the same time can serve the purpose of mechanically stabilizing the content of the container, for example against falling out of the cavity. The container can have at least one opening and/or at least one access which, as is explained in more detail below, is also designed such that it can be closed and which can allow access to the cavity. However, the size of the optional opening is not such that it negates the functions of the container, that is to say in particular the separation of the content from the environment and the mechanical stabilization and storage of the content.

A container differs to this extent from, for example, a simple suspension or a framework from which the content can easily fall out for lack of being enclosed. In particular, a container thus differs from a support frame as described, for example, in the abovementioned U.S. Pat. No. 7,104,074 B2 and EP 1 441 585 B1. Such support frames have no interior that is surrounded by a container wall and that performs the stated functions of shielding from the environment and of mechanical stabilization.

In the context of the present invention, a cryogenic container is generally to be understood as a container which is designed such that articles such as liquids and/or solids can be stored in the interior thereof at low temperatures, in particular at temperatures of below 0° C.

The cryogenic container comprises at least one primary container, which has at least one flexible film bag. A flexible film bag is to be understood as a device having at least one interior that receives the medium and that is preferably substantially closed. For example, this film bag can be designed as a rectangular film bag.

In the context of the present invention, flexibility is generally to be understood, as is normally the case in everyday language, as a deformability or bendability of a body. Unless other measurement conditions are specified, the term flexibility should, as is also generally the case, relate to a measurement carried out at room temperature and normal pressure. However, flexibility can also preferably be present at lower temperatures, for example at temperatures down to 5° C., preferably 0° C., and particularly preferably at still lower temperatures, for example down to −10° C., or even at temperatures lower than this, for example −20° C.

Flexibility of the film bag is to be understood as a flexibility property of the film bag that applies to the entire film bag or only to parts of this film bag, for example film walls of this film bag, and in which these flexible parts can undergo plastic or elastic deformation under the effect of a force. For example, this force can be a volume expansion of the actual medium that has been introduced into the inner space of the film bag, such that the walls of the flexible film bag deform.

The primary container is preferably designed at least partially as a disposable film bag. For example, standardized film bags as are customary in the area of biotechnology and medicine can be used for this purpose. Film bags of this kind can, for example, be made entirely or partially of plastic and can comprise one or more connectors, for example connectors for attachment of one or more tube connections. Examples are given in detail below.

The flexible film bag is designed to receive the medium and is preferably at least substantially leaktight, preferably completely leaktight.

The cryogenic container furthermore comprises at least one secondary container, which at least partially surrounds the primary container and which is also preferably at least partially flexible. A flexible design of the secondary container is to be understood as meaning that the latter can preferably adapt completely or partially to the shape of the filled primary container introduced into the secondary container. In this way, by adapting the secondary container to the primary container, it is possible to ensure particularly good heat transfer. The secondary container has at least one opening for insertion of the primary container. This opening can be permanently open, although it can also be designed such that it can be opened for the introduction and/or removal of the primary container into and/or from the interior of the secondary container and can otherwise preferably be closed.

The secondary container has at least one preferably at least partially flexible outer sleeve, that is to say an outer sleeve that can preferably undergo plastic or elastic deformation under the effect of a force. As regards the term flexibility, reference can be made generally to the above description of the term. The expression "at least partially flexible" is generally to be understood as a property of a body in which the latter is either completely flexible, i.e. flexible in all areas, or in which the body has at least one portion or area that is flexible and at least one further area or portion in which the body is not flexible.

The secondary container furthermore has at least one heat exchanger space, which is arranged between the outer sleeve and the flexible film bag and receives at least one fluid heat exchange medium. A heat exchanger space is to be understood as a gap between the primary container and the outer sleeve of the secondary container, through which gap the heat exchange medium can flow and/or in which gap the heat exchange medium can be held without flowing. The gap can be completely open, or it can also be closed at one end or at both ends. This gap is intended in particular to avoid direct contact between the primary container and the outer sleeve of the secondary container, without contact with the fluid heat exchange medium, and to preferably ensure a minimum spacing.

In particular, in order to completely or partially avoid such contact between the primary container and the outer sleeve, at least one spacer element can also be introduced into the heat exchanger space. This spacer element can be designed such that the fluid heat exchange medium can flow through it, and it can be configured to maintain a spacing between the outer sleeve and the film bag of the primary container.

The spacer element should preferably also be completely or partially flexible. Moreover, the spacer element should allow the fluid heat exchange medium to fill and/or flow through the heat exchanger space as uniformly and as completely as possible. It is preferable if the spacer element is made completely or partially of a plastic and has a plurality of channels and/or interstices through which the fluid heat exchange medium can flow. Alternatively or in addition to a plastic, however, other materials that have the above-mentioned properties are also possible in principle. For example, it is possible to use fillers between which, in the filled state, interstices are formed through which the heat exchange medium can flow. Alternatively or in addition, honeycomb structures can be used, for example, in which the honeycombs are interconnected, for example once again honeycomb structures made of plastic. Various configurations are possible.

The outer sleeve of the secondary container can be designed in various ways. For example, it can comprise a metal film and/or at least one film coated with a metallic material, in particular aluminium, for example a plastic film and/or paper film. A laminate film can also be used for example.

The cryogenic container can be designed such that the primary container is introduced directly into the secondary container with the outer sleeve and, if appropriate, with the spacer element. The gap between the primary container, for example the flexible film bag of the primary container, and the outer sleeve can then be filled with, or have flow through it, the at least one heat exchange medium, for example in order to ensure a freezing or thawing process as described in detail below. For example, the heat exchanger space can be filled directly with a gaseous heat exchange medium, for example a liquid gas, in particular nitrogen.

Alternatively or in addition, however, the secondary container can also have a more complex design. For example, the secondary container can furthermore have at least one inner sleeve, which faces the primary container and is preferably at least partially flexible. In turn, this inner sleeve can, for example, be made completely or partially of a plastic. The inner sleeve, like the outer sleeve too, is preferably substantially impervious with respect to the fluid heat exchange medium. Generally, the inner sleeve can have at least one film material, which can be present in coated or uncoated form. A laminate structure is also possible.

The cryogenic container can furthermore have at least one fluid heat exchange medium received in the heat exchanger space and/or flowing through the heat exchanger space. This heat exchange medium can in particular be one or more of the following heat exchange media: a silicone oil; a gas (i.e. a medium that is gaseous under normal conditions) in a liquid and/or gaseous state, in particular a liquid gas, in particular nitrogen, particularly preferably liquid nitrogen. The use of liquid nitrogen in particular is particularly inexpensive and can allow simple and inexpensive freezing of the medium. It has been found in tests that commercially available film bags, for example the bags described above, which are generally also available as disposable materials, withstand the temperatures of the liquid nitrogen.

Particularly when the abovementioned inner sleeve is used, the secondary container can be designed at least partially as a flexible and at least two-walled receiving bag. A receiving bag is to be understood as a bag that has an interior and at least one opening for introduction of the primary container into the interior. The receiving bag can have two or more walls. These walls comprise the at least one outer sleeve and also at least one preferably at least partially flexible inner sleeve facing the film bag, for example according to the above description. The two-walled receiving bag furthermore comprises at least one heat exchanger space arranged between the outer sleeve and the inner sleeve, for example according to the above description. The at least one spacer element according to the above description can in turn be optionally introduced into this heat exchanger space.

The outer sleeve and the inner sleeve are to be connected to each other in at least one area, in such a way that the heat exchanger space is at least substantially closed off. Substantially closed off is to be understood as an at least substantially media-tight closure with respect to the heat exchange medium, such that this heat exchange medium cannot accidentally get into the interior of the receiving bag and/or get outside the receiving bag, at least not during conventional storage periods of 1 to 2 years. Fairly small leakages, however, can be tolerated.

The receiving bag can furthermore have at least one delivery device for the heat exchange medium. In particular, the receiving bag can have a first connector, in particular at least one connector nozzle, for delivery of the heat exchange medium and preferably at least one second connector, in particular a connector nozzle, for removal of the heat exchange medium. The first connector and the second connector are to be fluidically connected to the heat exchanger space. At least one channel through which the heat exchange medium can flow is to be formed in the heat exchanger space between the first connector and the second connector. This channel can be flat and broad and can also be branched or designed with a plurality of channels. This channel is preferably designed in such a way that, in the area where the receiving bag surrounds the primary container, the channel is complete, such that uniform temperature control of the primary bag is possible.

The secondary container can furthermore have at least one element controlling and/or regulating a filling level of the heat exchange medium in the heat exchanger space. For example, this element can comprise a sensor and/or a valve. For example, a float valve can be provided, which limits a filling level of the heat exchange medium in the heat exchanger space or adjusts it to a defined level.

In addition to the primary container and the secondary container, the cryogenic container can furthermore have at least one substantially dimensionally stable outer container. The expression "substantially dimensionally stable" is to be understood as a property by which, under the normal loads that arise during transport, for example under the inherent weight and/or the weight of the contents, there is no appreciable deformation of the outer container. The outer container is to be designed to receive the at least one secondary container, with the at least one primary container received therein, and to shield them against external mechanical action. Shielding is to be understood as a property by which external forces normally arising during transport cannot cause damage to the secondary container and/or the primary container. For example, the outer container can be made completely or partially from a stiff material.

The outer container can have one or more interiors in which the secondary container or secondary containers can be inserted. An individual interior can be provided in which one or more secondary containers are received with one or more primary containers. Alternatively, however, a plurality of interiors can also be provided, for example by the outer container being divided into corresponding compartments. One secondary container or a plurality of secondary containers can be received in each of these compartments, in each case with one or more primary containers.

The outer container can furthermore have thermally insulating properties. Thermally insulating properties are to be understood as meaning a delay in temperature equalization to a surrounding area, such that, for example, a frozen state of an aqueous medium in the interior of the outer container can be maintained even at room temperature for several minutes, without active cooling measures, and preferably for several hours. These thermally insulating properties can be achieved, for example, by the use of one or more thermally insulating materials, for example foamed materials and/or paper or cardboard materials.

For example, the outer container can be made completely or partially of a paper material, in particular comprising a corrugated board. However, other materials can also be used in principle. The materials of the outer container are preferably completely or partially designed such that they can be easily disposed of, with the result that the cryogenic container can preferably be designed as a whole as a disposable cryogenic container, if appropriate with the exception of a few elements that can be reused. Paper material in particular is easy to dispose of and is therefore environmentally friendly.

The outer container can, for example, have what is substantially a cuboid shape. A substantially cuboid shape is to be understood as a shape that can also deviate slightly from a perfect cuboid shape. For example, one or more support elements can be provided on the outer container in order to increase the stability of the outer container. Alternatively or in addition, connecting elements can also be provided in order to permit stable interconnection of a plurality of outer containers, for example by hooking, and/or to be able to accommodate a plurality of outer containers comfortably on a pallet.

The outer container can furthermore have a substantially closed design. For this purpose, the outer container can, for example, have a body with a corresponding recess and several lids. Another design is also possible. Moreover, the cryogenic container can have at least one passage for the introduction and/or removal of the at least one heat exchange medium and/or of the medium itself. These passages can, for example, comprise simple openings. Alternatively or in addition, more complex passages are also possible. For example, tube passages, if appropriate with at least one corresponding connector. Various embodiments are conceivable.

In addition to the cryogenic container, these teachings also propose a secondary container for use in a cryogenic container according to one or more of the above-described embodiments. Regarding the possible configurations of the secondary container, reference can be largely made to the above description. Thus, the secondary container is preferably at least partially flexible and has at least one opening for insertion of the primary container. The secondary container furthermore has at least one preferably at least partially flexible outer sleeve, and also at least one heat exchanger space, which is arranged between the outer sleeve and the flexible primary container, in particular the flexible film bag of the primary container, and receives at least one fluid heat exchange medium. For further embodiments, reference can be made to the above description.

These teachings furthermore propose a preparation device for storage of a medium, in particular a biochemical and/or medical product. For the description of this medium, reference can largely be made to the above description. A preparation device for storage of the medium is to be understood as a device in which the medium is prepared for storage, is made ready for use again after storage, is made ready for transport or is made ready for use again after transport. For example, this preparation device can be suitable for freezing and/or thawing the medium.

The preparation device comprises at least one cryogenic container according to one or more of the above-described embodiments. The preparation device furthermore comprises at least one supply device that can be coupled reversibly to the cryogenic container for supplying a heat exchange medium to the cryogenic container. For example, the supply device can comprise a device for cooling and/or heating the heat exchange medium. Furthermore, the supply device can alternatively or in addition comprise at least one pump for introducing the heat exchange medium into the secondary container and/or for pumping it through the secondary container. A reversible coupling is to be understood as meaning that, for example by way of a tube connection and/or a similar detachable connection, heat exchange medium can be temporarily supplied to the cryogenic container and/or pumped through the latter. For transport of the cryogenic container and/or for storage of the cryogenic container, the preparation device can then be completely or partially uncoupled from the cryogenic container, for example with some of the heat exchange medium remaining in the secondary container.

In addition to the above-described devices in one or more of the above-described embodiments, disclosed is a method for storing and/or transporting a medium, in particular a biochemical and/or medical product, which method can in particular use a cryogenic container as claimed in one of the preceding claims relating to a cryogenic container. Furthermore, a secondary container and/or a preparation device according to one or more of the above-described embodiments can be used, such that reference can likewise be largely made to the above description.

The method comprises the method steps described below. These method steps can be carried out in the sequence indicated, although this is not strictly necessary. For example, the first method step described below and the second method step described below can be carried out in reverse. Moreover, other method steps (not indicated) can be carried out. Moreover, method steps can be carried out in another sequence, or individual method steps or several method steps can be repeated, overlapping in time or simultaneously.

In a first method step, a primary container is introduced into a secondary container, wherein the primary container has at least one flexible film bag, wherein the secondary container is preferably at least partially flexible and has at least one opening for insertion of the primary container. The secondary container furthermore has at least one preferably at least partially flexible outer sleeve and at least one heat exchanger space, which is arranged between the outer sleeve and the flexible film bag of the primary container and receives at least one fluid heat exchange medium. In a second method step, the medium is introduced into the primary container, for example by simple filling, pumping, pouring, or by other methods known to a person skilled in the art and preferably adapted to the properties of the medium. It will be noted that the primary container can be introduced into the secondary container before or after the primary container is filled with the medium. In view of the lower risk posed by handling, a method is generally preferred in which the primary container is filled with the medium when this primary container is already located in the secondary container.

In a third method step, at least one heat exchange medium is conveyed into or through the heat exchanger space. This introduction of the heat exchange medium into the heat exchanger space can be done in a single filling operation. Alternatively, as has been indicated above with reference to the possible configurations of the secondary container, the heat exchange medium can also be conveyed through the heat exchanger space, for example by being circulated by pumping.

The method can be advantageously developed in various ways. For example, in a further method step, the secondary container can be introduced into a substantially dimensionally stable outer container, in which respect reference can once again be made to the above description. The outer container is designed to receive the at least one secondary container, with the at least one primary container received therein, and to shield it against external mechanical action. Once again, the secondary container can be introduced into the outer container at a time when the primary container is already contained in the secondary container. Alternatively, however, it is also possible for the unfilled secondary container first to be introduced into the outer container, after which the primary container is introduced into the outer container.

In a further method step, the medium can be frozen and then stored and/or transported. For the freezing, a heat exchange medium with a temperature below a freezing point of the medium can be used, for example, as has been indicated above, silicone oil and/or a liquid gas, for example liquid nitrogen. As has been indicated above, the heat exchange medium can be introduced all at once and/or pumped through the cryogenic container. Combinations are also possible, for example by heat exchange medium being introduced all at once, and this then being topped up if necessary, that is to say replenished. A cooling circuit can be provided, in which case the primary container, with the medium received therein, is cooled by the heat exchange medium in one area, and in which case, in another area, the heat exchange medium ensures that the heat absorbed during cooling is transferred to another medium and/or another device. It will be noted in this connection that the expression heat exchange medium is to be understood broadly in the context of the present invention and includes any fluid medium that is able to take up heat and in this way cool the medium that is to be stored and/or transported. The heat exchange medium can, for example, be part of a fluid medium of a heat pump or can be used in another way to cool the medium that is to be stored and/or transported.

In order to thaw the medium again after it has been stored and/or transported, the method can furthermore involve introducing a gaseous and/or liquid heat exchange medium with a temperature above a freezing point of the medium. This heat exchange medium, which acts here as a thawing medium, can, for example, again be introduced all at once, or, as is preferred, pumped through the secondary container. The heat exchange medium can in this case also be heated air, for example, which is blown into the outer container, for example with the aid of a fan. Other heated gases and/or heated liquids can also be used.

The method can furthermore comprise at least one method step in which the primary container and/or the secondary container and also, if appropriate, the optional outer container are completely or partially disposed of after the medium has been removed. This disposal can be done, for example, by complete or partial recycling and/or burning.

The proposed devices and the proposed method in one or more of the above-described embodiments have numerous advantages over known devices and methods. For example, the freezing and/or thawing of the medium can take place in a heat exchanger which, after the process, can also be disposed of completely. Although cleaning and/or sterilization can additionally be carried out if appropriate, this is not generally necessary.

In contrast to stainless steel cryogenic containers, which require considerable investment and considerable outlay in terms of logistics, the proposed cryogenic containers and the proposed method require comparatively low investment costs and/or running costs since they are used just once. Moreover, the proposed cryogenic containers and/or the proposed method do not generally tie up capital. Adaptation to modified volumes and/or process conditions is also easier. For heat transfer, it is possible to use inexpensive heat exchange media, for example nitrogen, in particular liquid nitrogen. The cryogenic containers can be produced in a compact form, such that a relatively small refrigeration surface area is necessary, in contrast to known cryogenic containers made of stainless steel, for example. Transport costs can also be reduced considerably. This is because the proposed cryogenic containers can be made considerably lighter than conventional cryogenic containers. Moreover, the cryogenic containers are inexpensive and can be designed as disposable cryogenic containers, such that return shipment of the empty cryogenic containers is not generally required. The empty cryogenic containers can be disposed of in situ.

Moreover, the proposed cryogenic containers, when empty, can also be stored taking up a small volume. In particular, the use of paper materials also permits folding for storage purposes, such that the storage costs can be reduced considerably by comparison with conventional stainless steel containers. It is also possible to react flexibly to changes in capacity requirements.

Moreover, since it is possible to avoid using heat exchange media that are difficult to handle, for example silicone oil, there is much less risk of contamination. In particular, the use of liquid nitrogen offers the possibility of high process safety, with at the same time considerably reduced costs. The one-off introduction of a heat exchange medium, for example a precisely measured amount of a heat exchange medium for one freezing operation, is easy to do, especially when using nitrogen as heat transfer medium, since nitrogen is inexpensive and widely available.

By using disposable cryogenic containers and/or using cryogenic containers that are designed at least partially as disposable cryogenic containers, the cleaning costs and/or plant investments that arise in the case of stainless steel cryogenic containers can also be avoided. Disposing of the cryogenic containers is also in many cases more environmentally friendly than complicated cleaning, for example with cleaning agents and/or disinfecting agents. It is also possible to ensure a high degree of sterility, and the danger of cross-contamination can be avoided. The environmentally friendly nature of the entire process can be further improved by the fact that, by disposing of the cryogenic containers, there is no need for their return shipment, since they are designed to be easy and inexpensive to dispose of.

Compared to known disposable cryogenic containers, for example the containers described in EP 1 441 585 B1 and U.S. Pat. No. 7,104,074 B2, the proposed design has the advantage of the provision of the secondary container, in which the heat exchange medium can be contained and which can protect the primary container from mechanical damage. To provide further mechanical protection, the above-described at least one outer container can be provided, which can protect the primary container and/or also the secondary container from mechanical loads. The secondary container can at the same time act as an integrated, yet disposable heat exchanger, such that the cryogenic container is also suitable for at least brief transportation outside a refrigeration area and/or refrigeration container. At the same time, however, this integrated heat exchanger can be implemented in a space-saving and inexpensive manner, such that it can also be easily disposed of and does not require return shipment.

BRIEF DESCRIPTION OF THE DRAWINGS

Further details and features are set forth in the following description of preferred illustrative embodiments. The respective features can be implemented singly, or several of them in combination with one another. The invention is not limited to the illustrative embodiments. The illustrative embodiments are depicted schematically in the figures. The same reference signs in the individual figures designate identical elements or designate elements that have an identical function or that correspond in terms of their functions.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
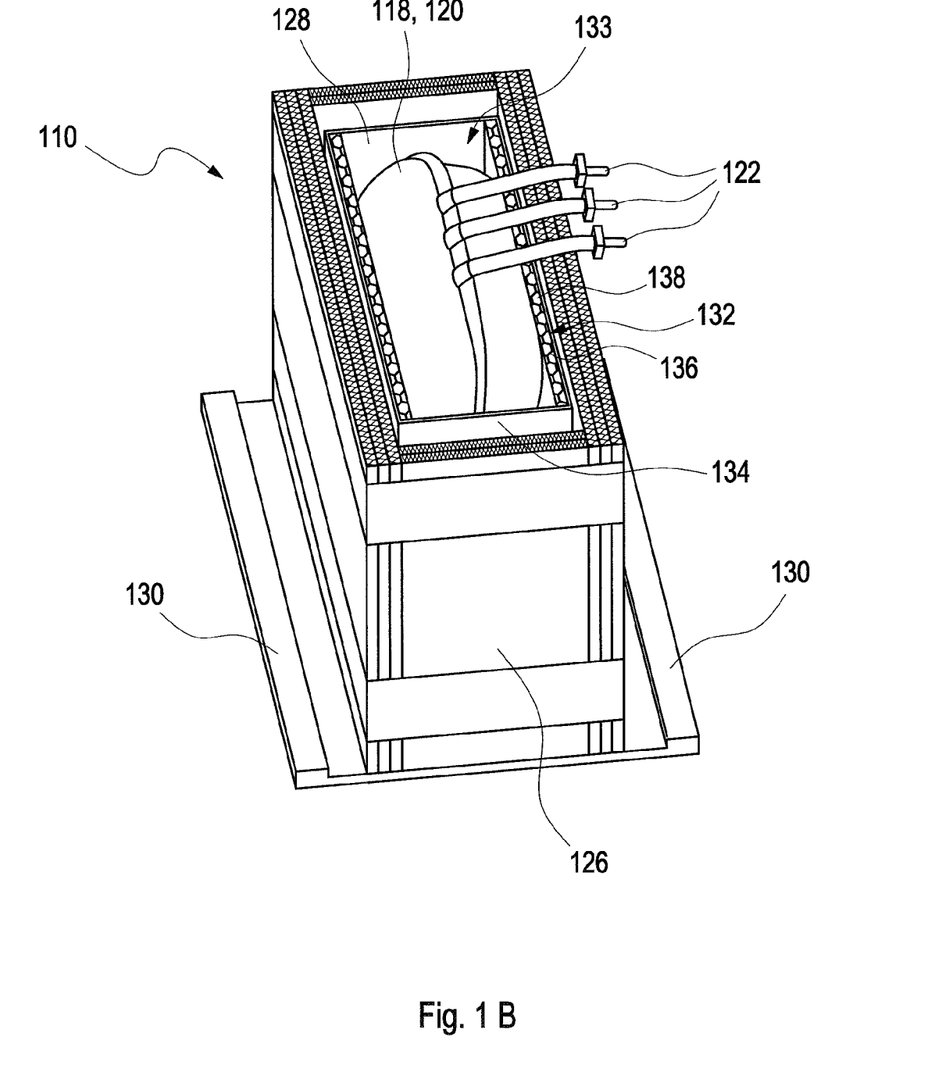
FIG. 1A shows a sectional view of a first illustrative embodiment of a cryogenic container according to the invention.
FIG. 1B shows a perspective view of the cryogenic container according to FIG. 1A, in a plan view seen obliquely from above.
FIG. 1C shows a plan view of the cryogenic container according to FIG. 1A.
Figure 1A:
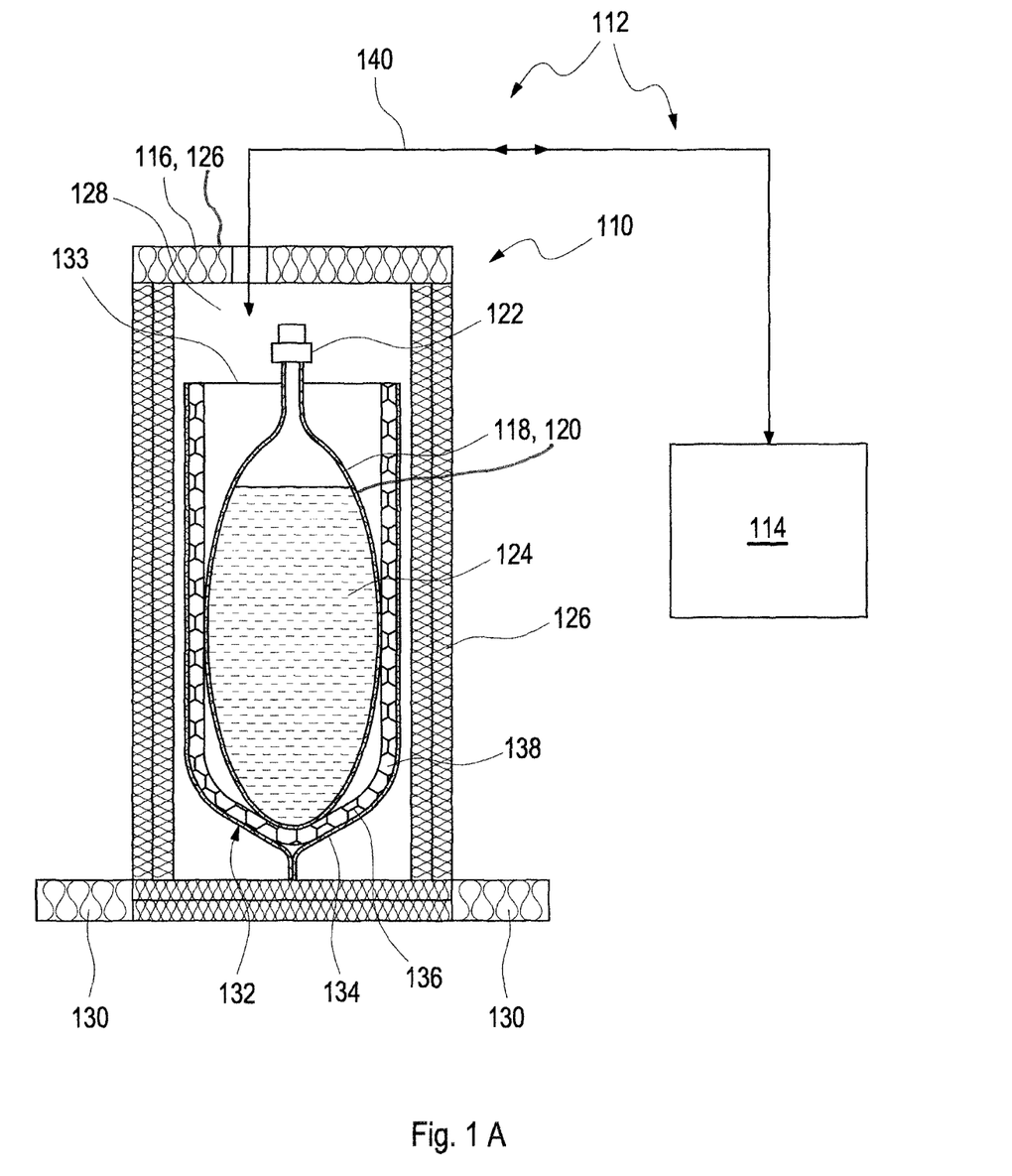

A first illustrative embodiment of a cryogenic container 110 is shown in FIGS. 1A to 1C. At the same time, FIG. 1A shows an illustrative embodiment of a preparation device 112, which preparation device 112 furthermore comprises, in addition to the cryogenic container, a supply device 114 that can be coupled reversibly to the cryogenic container 110. FIGS. 1B and 1C show only the cryogenic container 110, the latter being shown in FIG. 1A in a sectional view from the side with a lid 116, in a perspective view obliquely from above and without lid 116 (FIG. 1B), and in a perspective view from above and without lid 116 (FIG. 1C).

The cryogenic container 110 comprises a primary container 118 in the form of a flexible film bag 120 with tube connectors 122. For example, this flexible film bag 120 can be designed as a sterilized disposable bag, for example as a "Standard Flexboy® bioprocessing bag" from Sartorius Stedim Biotech. However, other designs are also possible in principle. The primary container 118 can be filled with a medium, for example a medicament, a diagnostic agent or a biotechnical material, via the tube connectors 122, which can be designed as sterile connections. The medium is designated generally in the Figs. by reference sign 124.

Furthermore, the cryogenic container 110 comprises an outer container 126 which, in this illustrative embodiment, can be produced from a basic framework composed of a simple supporting material, for example multi-layer corrugated board. This basic framework serves at the same time for stabilization and insulation. As is shown in FIGS. 1A to 1C, the outer container 126 can be substantially cuboid, for example, with an interior 128 and, optionally, with one or more support devices 130 for increasing the stability.

In the illustrative embodiment shown in FIGS. 1A to 1C, a secondary container 132 is introduced into this framework of the outer container 126. In the illustrative embodiment shown, this secondary container 132 is open at its upper end and has an opening 133 through which the flexible film bag 120 of the primary container 118 can be introduced into the secondary container 132. In the illustrative embodiment, the secondary container 132 has an outer sleeve 134, which is flexible. This outer sleeve 134 can, for example, be a bag that is open at the top and that is made of aluminium film and/or of a metal-coated plastic film, for example an aluminium-coated plastic film. A spacer element 136 is fitted in this outer sleeve 134, which spacer element 136 at the same time serves for stiffening and for forming a heat exchanger space 138 between the outer sleeve 134 and the flexible film bag 120 of the primary container 118. This spacer element 136 can be made of plastic, for example. This can ensure a separating layer between the insulation, in particular the secondary container 132 or the outer sleeve 134, and the medium 124. As can be seen in particular from FIG. 1C, this spacer element 136, in the illustrative embodiment shown, is arranged only on the broad sides of the flexible film bag 120, not on the narrow sides. On these narrow sides, therefore, there is only slight contact, if any, between the outer sleeve 134 and the primary container 118.

The spacer element 136 is designed such that it can receive a heat exchange medium or can have a heat exchange medium flow through it. For example, after the primary container 118 has been filled with the medium 124, it is possible for liquid nitrogen ($LN_2$), for example, to be introduced into the gap serving as heat exchanger space 138 between the outer sleeve 134 and the flexible film bag 120. This liquid nitrogen evaporates spontaneously and thus cools the medium 124. The process can be controlled via the quantity of liquid nitrogen. For example, as is shown in FIG. 1A, the liquid nitrogen can be supplied from a supply device 114 via a conduit system 140, which is not shown in the other figures and which can be coupled to the cryogenic container 110 and uncoupled therefrom. After the process of freezing the medium 124, for example at −25° C., has been completed, the whole disposable system of the cryogenic container 110 can be stored in a refrigeration room, for example.

At the end of the storage period, pre-heated air, for example, is blown into the heat exchanger space 138 in order to thaw the medium 124 and return the latter to a state ready for use. This too can be done, for example, by means of the supply device 114 or a similar supply device. Alternatively or in addition to active thawing, for example in the manner described, it is also possible to use a passive thawing process. For example, the surrounding air at room temperature can itself suffice to permit thawing without auxiliary devices and/or without pre-heated air being actively blown into the heat exchanger space 138.

The process involved means that very rapid freezing times are possible with the system shown. This is particularly advantageous in the case of biological or biochemical media 124 in which, for example, a slow freezing and thawing process could lead to phase separation or other lack of homogeneity After use, the inexpensive cryogenic container can be completely or partially disposed of without special cleaning. Shipment of containers to and fro, as is generally required in the case of conventional cryogenic containers made of stainless steel, can therefore preferably be avoided.

Commercially available disposables can be used, for example, as the flexible film bag 120. Bag volumes of up to 50 liters or even 80 liters or more are conceivable, for example. It is also possible to use multiple sets, that is to say cryogenic containers 110 with a plurality of primary containers 118, for example in one or more interiors 128. For example, a plurality of compartments can be provided. For example, one, two, three, four or five flexible film bags 120 can be received in one cryogenic container 110. For example, several cryogenic containers 110 can be stored on a pallet, for example a Euro pallet. In particular, up to 300 liters can be stored on one pallet, with half the weight and volume compared to conventional cryogenic vessels, particularly of stainless steel.

In initial tests, the proposed cryogenic container has proven feasible for practical use. Thus, for example, freezing times of about half an hour were recorded for one liter of water. Between 1.5 and 2 liters of liquid nitrogen were needed per kilogram of liquid. For example, a predetermined quantity of liquid nitrogen that is just sufficient for one freezing process can be fed into the heat exchanger space 138.

Figure 2:
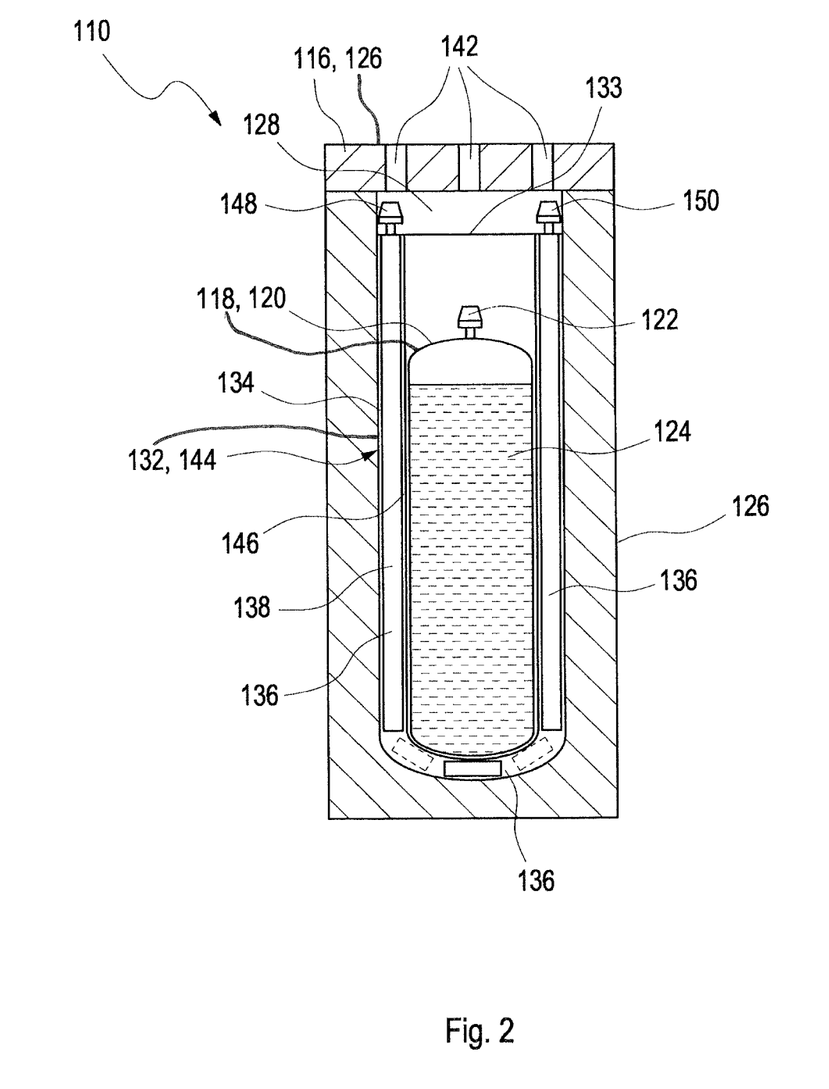
FIG. 2 shows a view, analogous to FIG. 1A, of a second illustrative embodiment of a cryogenic container according to the invention.

FIG. 2, in a view analogous to FIG. 1, but without the supply device 114 and the conduit system 140, shows a second embodiment of a cryogenic container 110 according to the invention. This cryogenic container 110 again comprises a primary container 118 with a flexible film bag 120 and tube connectors 122. As regards this primary container 118, reference can be made for example to the above description of FIGS. 1A to 1C.

Furthermore, the cryogenic container 110 once again comprises an outer container 126, which also has a lid 116. This lid 116 is in this case provided with a plurality of passages 142, such that the heat exchange medium and/or the medium 124 that is to be stored and transported can be introduced and/or removed even when the outer container 126 is closed. As regards the possible designs of the outer container 126, reference can be made for example to the above description of FIGS. 1A to 1C.

Once again, the cryogenic container 110 also has a secondary container 132, which has a heat exchanger space 138. However, in contrast to the illustrative embodiment according to FIGS. 1A to 1C, the heat exchange medium in the illustrative embodiment according to FIG. 2 is preferably not in direct contact with the flexible film bag 120, which can be designed as a plastic bag, for example. For this purpose, the secondary container 132 in the illustrative embodiment shown is designed with a two-walled receiving bag 144. Thus, the secondary container 132 has, in addition to the outer sleeve 134, also a flexible inner sleeve 146 facing the flexible film bag 120. The outer sleeve 134 and the inner sleeve 146 can be welded to each other at the edges, such that a heat exchanger space 138 in the form of a long, narrow and broad channel is formed between the outer sleeve 134 and the inner sleeve 146, which heat exchanger space 138 begins at a first connector 148 and ends at a second connector 150. The first connector 148 can accordingly serve as an inlet for a heat exchange medium, and the second connector 150 as an outlet for this heat exchange medium. In the gap between the inner sleeve 146 and the outer sleeve 134, that is to say in the heat exchanger space 138, which again can also be filled with, for example, a stiff spacer element 136, the heat exchange medium can flow from the first connector 148 to the second connector 150. The spacer element 136 can in addition act completely or partially as a flow-directing means, in order to ensure a uniform through-flow, preferably along the entire surface of the heat exchanger space 138.

The heat exchange medium can be pumped through the heat exchanger space 138 from the first connector 148 to the second connector 150, for example by means of a corresponding supply device 114 according to FIG. 1A. As heat exchange medium, that is to say as heat transfer medium, silicone oil, for example, can be used in this case.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS 110 cryogenic container
112 preparation device
114 supply device
116 lid
118 primary container
120 flexible film bag
122 tube connectors
124 medium
126 outer container
128 interior
130 support devices
132 secondary container
133 opening
134 outer sleeve
136 spacer element
138 heat exchanger space
140 conduit system
142 passages
144 two-walled receiving bag
146 inner sleeve
148 first connector
150 second connector

What is claimed is:

1. A cryogenic container for storing and/or transporting a medium, comprising:
    a primary container formed as a flexible film bag configured to receive the medium; and
    a secondary container at least partially surrounding the primary container, wherein the secondary container is at least partially flexible and has at least one openable and closable opening through which the primary container is configured to be inserted into and removed from the secondary container, wherein the secondary container is configured to adapt completely or partially to the shape of the filled primary container introduced into the secondary container, the secondary container comprising an at least partially flexible outer sleeve and an at least partially flexible inner sleeve and a heat exchanger space arranged between the outer sleeve and the inner sleeve, the inner sleeve contacting the flexible film bag, the heat exchanger space comprising an enclosed channel between the outer sleeve and the inner sleeve for receiving a fluid heat exchange material for freezing and/or thawing the medium, and wherein the secondary container comprises at least one first connector for delivery of the fluid heat exchange material to the channel and at least one second connector for removal of the fluid heat exchange material from the channel, whereby the fluid heat exchange material is configured to flow through the channel and around the primary container.

2. The cryogenic container of claim 1, wherein the primary container comprises a disposable film bag.

3. The cryogenic container of claim 1, wherein the heat exchanger space comprises a spacer element arranged therein, wherein the spacer element is configured to permit the fluid heat transfer material to flow through the spacer element, and wherein the spacer element maintains a spacing between the outer sleeve and the flexible film bag.

4. The cryogenic container of claim 1, wherein the outer sleeve of the secondary container comprises at least one metal film and/or at least one plastic film and/or a paper film coated with a metallic material.

5. The cryogenic container of claim 1, wherein the outer sleeve and the inner sleeve are connected to each other in at least one area to close off the heat exchanger space.

6. The cryogenic container of claim 1, wherein the secondary container further comprises an element that controls or regulates filling of the heat exchanger space.

7. The cryogenic container of claim 6, wherein the element comprises a float valve.

8. The cryogenic container of claim 1, further comprising a substantially dimensionally stable outer container, wherein the outer container receives the secondary container having the primary container received in the secondary container, the outer container shielding the secondary and primary containers from external mechanical action.

9. The cryogenic container of claim 8, wherein the outer container comprises a corrugated board.

10. The cryogenic container of claim 1, wherein the first connector is configured to reversibly couple the cryogenic container to at least one supply device for supplying the fluid heat exchange material to the cryogenic container.

11. A method for storing and/or transporting a medium using a cryogenic container, comprising:
   providing a primary container formed as a flexible film bag configured to receive the medium;
   providing an at least partially flexible secondary container having a flexible outer sleeve an at least partially flexible inner sleeve, and an opening through which the primary container is configured to be inserted into and removed from the secondary container;
   inserting the primary container into the interior space of the secondary container through the opening such that the secondary container at least partially surrounds the primary container;
   arranging a heat exchanger space between the flexible outer sleeve and the inner sleeve, the inner sleeve contacting the flexible film bag, the heat exchanger space comprising an enclosed channel between the outer sleeve and the inner sleeve for receiving a fluid heat exchange material for freezing and/or thawing the medium;
   introducing the medium into the primary container, wherein the secondary container adapts completely or partially to the shape of the primary container introduced into the secondary container; and
   conveying a heat exchange material into or through the heat exchanger space for freezing and/or thawing the medium;
   wherein the secondary container comprises at least one first connector for delivery of the fluid heat exchange material to the channel and at least one second connector for removal of the fluid heat exchange material from the channel, whereby the fluid heat exchange material is configured to flow through the channel and around the primary container.

12. The method of claim 11, further comprising introducing the secondary container into at least one substantially dimensionally stable outer container, whereby the outer container shields the secondary container with the primary container received therein against external mechanical action.

13. The method of claim 11, further comprising freezing and then storing and/or transporting the medium, wherein the heat transfer medium conveyed has a temperature below the freezing point of the medium.

14. The method of claim 13, further comprising, after the storing and/or transporting of the medium, introducing into the heat exchanger space a second heat transfer material with a temperature above the freezing point of the medium.

15. The method of claim 11, further comprising removing the medium from the primary container and then disposing of the primary container and/or the secondary container and/or an outer container.

16. A secondary container for use in a cryogenic container having a primary container formed as a flexible film bag configured to receive a medium, the secondary container comprising:
   an at least partially flexible material and having at least one openable and closable opening through which the primary container is configured to be inserted into and removed from the secondary container;
   an at least partially flexible outer sleeve and an at least partially flexible inner sleeve;
   wherein, when the primary container is placed in the secondary container:
      (a) a heat exchanger space is formed between the outer sleeve and the inner sleeve, the inner sleeve contacting the flexible film bag, the heat exchanger space comprising an enclosed channel between the outer sleeve and the inner sleeve for receiving at least one fluid heat exchange material for freezing and/or thawing the medium; and
      (b) the secondary container adapts completely or partially to the shape of the filled primary container;
   and wherein the secondary container comprises at least one first connector for delivery of the fluid heat exchange material to the channel and at least one second connector for removal of the fluid heat exchange material from the channel, whereby the fluid heat exchange material is configured to flow through the channel and around the primary container.

17. The secondary container of claim 16, wherein the outer sleeve comprises at least one metal film and/or at least one plastic film and/or a paper film coated with a metallic material.

18. A cryogenic container for storing and/or transporting a medium, comprising:
   a primary container having a flexible film bag configured to receive the medium; and
   a secondary container at least partially surrounding the primary container, wherein the secondary container is at least partially flexible and has at least one openable and closable opening through which the primary container is configured to be inserted into the secondary container, the secondary container comprising an at least partially flexible outer sleeve and a heat exchanger space arranged between the outer sleeve and the flexible film bag for receiving a fluid heat transfer material, wherein the heat exchanger space comprises a spacer element arranged therein, the spacer element being configured to permit the fluid heat transfer material to flow through the spacer element while the spacer element spaces the outer sleeve from the outer periphery of the flexible film bag.

19. The cryogenic container of claim 18, wherein the spacer element contacts a wall of the secondary container to maintain the spacing between the outer sleeve and the flexible film bag.

20. A method for storing and/or transporting a medium using a cryogenic container, comprising:
   providing a primary container having at least one flexible film bag configured to receive the medium;
   providing an at least partially flexible secondary container having a flexible outer sleeve and an opening through which the primary container is configured to be inserted into the secondary container;

inserting the primary container into the secondary container through the opening such that the secondary container at least partially surrounds the primary container;

closing the opening of the secondary container;

arranging a heat exchanger space between the flexible outer sleeve and the flexible film bag and arranging a spacer element in the heat exchanger space;

introducing the medium into the primary container; and conveying a heat transfer material into or through the heat exchanger space, wherein the spacer element permits the fluid heat transfer material to flow through the spacer element while the spacer element spaces the outer sleeve from the outer periphery of the flexible film bag.

21. The method of claim 20, wherein the spacer element contacts a wall of the secondary container to maintain the spacing between the outer sleeve and the flexible film bag.

22. A secondary container for use in a cryogenic container having a primary container having a flexible film bag configured to receive a medium, the secondary container comprising:

an at least partially flexible material and having at least one openable and closable opening through which the primary container is configured to be inserted into the secondary container;

an at least partially flexible outer sleeve; and a spacer element;

wherein, when the primary container is placed in the secondary container, a heat exchanger space is formed between the outer sleeve and the primary container for receiving at least one fluid heat transfer material and the spacer element permits the fluid heat transfer material to flow through the spacer element while the spacer element spaces the outer sleeve from the outer periphery of the flexible film bag.

23. The secondary container of claim 22, wherein the spacer element contacts a wall of the secondary container to maintain the spacing between the outer sleeve and the flexible film bag.

* * * * *